United States Patent
Sui et al.

(10) Patent No.: US 11,141,138 B2
(45) Date of Patent: Oct. 12, 2021

(54) KALMAN FILTERING FOR FLASH ARTIFACT SUPPRESSION IN ULTRASOUND IMAGING

(71) Applicant: Siemens Medical Solutions USA, Inc., Malvern, PA (US)

(72) Inventors: Lei Sui, Medina, WA (US); Kathryn Ozgun, Finksburg, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 346 days.

(21) Appl. No.: 16/423,235

(22) Filed: May 28, 2019

(65) Prior Publication Data

US 2020/0375575 A1 Dec. 3, 2020

(51) Int. Cl.
*A61B 8/06* (2006.01)
*A61B 8/08* (2006.01)

(52) U.S. Cl.
CPC .............. *A61B 8/5276* (2013.01); *A61B 8/06* (2013.01); *A61B 8/488* (2013.01)

(58) Field of Classification Search
CPC .......... A61B 8/06; A61B 8/188; A61B 8/5276
See application file for complete search history.

(56) References Cited

U.S. PATENT DOCUMENTS

| | | | |
|---|---|---|---|
| 5,152,292 A * | 10/1992 | Karp | G01S 7/52071 600/443 |
| 5,197,477 A | 3/1993 | Peterson | |
| 5,245,436 A | 9/1993 | Alattar | |
| 5,782,769 A | 7/1998 | Hwang | |
| 6,217,520 B1 | 4/2001 | He | |
| 6,287,258 B1 * | 9/2001 | Phillips | G01S 7/52046 600/437 |
| 6,760,486 B1 | 7/2004 | Chiao | |
| 8,740,798 B2 | 6/2014 | Hamada | |
| 8,864,671 B2 | 10/2014 | Ma | |
| 8,870,777 B2 | 10/2014 | Miyama | |
| 9,320,498 B2 * | 4/2016 | Seo | A61B 8/5269 |
| 9,420,997 B2 * | 8/2016 | Wong | A61B 8/5223 |
| 2007/0167795 A1 | 7/2007 | Hyun | |
| 2009/0227868 A1 | 9/2009 | Dong | |
| 2012/0136243 A1 | 5/2012 | Boese | |
| 2015/0250446 A1 | 9/2015 | Kanayama | |
| 2015/0327838 A1 * | 11/2015 | Francis | A61B 8/5276 600/450 |

(Continued)

FOREIGN PATENT DOCUMENTS

| | | |
|---|---|---|
| EP | 0871043 A2 | 10/1998 |
| JP | H04218143 A | 8/1992 |
| JP | H1075955 A | 3/1998 |
| JP | 3029315 B2 | 4/2000 |

(Continued)

OTHER PUBLICATIONS

Bishop, Gary, and Greg Welch. "An introduction to the Kalman filter." Proc of SIGGRAPH, Course 8.27599-3175 (2001): 59.

(Continued)

*Primary Examiner* — Boniface N Nganga (57) ABSTRACT

Kalman filtering, including a model of system dynamics, is used to identify flash artifact. The Kalman filtering predicts the velocity or powers based on a past sequence of velocity or power. The prediction defines a confidence interval. Any current measures surpassing the confidence interval are identified as flash artifact and suppressed.

20 Claims, 5 Drawing Sheets

(56) References Cited

U.S. PATENT DOCUMENTS

| | | |
|---|---|---|
| 2015/0359507 A1 | 12/2015 | Shibata |
| 2015/0379700 A1 | 12/2015 | Kamiyama |
| 2016/0058425 A1 | 3/2016 | Wong |

FOREIGN PATENT DOCUMENTS

| | | | | |
|---|---|---|---|---|
| JP | 2018033670 A | 3/2018 | | |
| WO | WO-0173470 A1 | * | 10/2001 | ......... G01S 7/52046 |
| WO | WO-2018197254 A1 | * | 11/2018 | ........... A61B 8/5207 |

OTHER PUBLICATIONS

Bjaerum, Steinar, Hans Torp, and Kjell Kristoffersen. "Clutter filters adapted to tissue motion in ultrasound color flow imaging." IEEE transactions on ultrasonics, ferroelectrics, and frequency control 49.6 (2002): 693-704.

Fadnes, Solveig, et al. "Clutter filtering influence on blood velocity estimation using speckle tracking." IEEE transactions on ultrasonics, ferroelectrics, and frequency control 62.12 (2015): 2079-2091.

Heimdal, Andreas, and Hans Torp. "Ultrasound Doppler measurements of low velocity blood flow: limitations due to clutter signals from vibrating muscles." IEEE transactions on ultrasonics, ferroelectrics, and frequency control 44.4 (1997): 873-881.

Kalman, Rudolph Emil. "A new approach to linear filtering and prediction problems." Journal of basic Engineering 82.1 (1960): 35-45.

Mobinder, S. Grewal, and P. Andrews Angus. "Kalman filtering theory and practice using matlab." (2001).

Rubin, Jonathan M., et al. "Power Doppler US: a potentially useful alternative to mean frequency-based color Doppler US." Radiology 190.3 (1994): 853-856.

Tierney, Jaime, et al. "Adaptive Clutter Demodulation for Non-Contrast Ultrasound Perfusion Imaging." IEEE transactions on medical imaging 36.9 (2017): 1979-1991.

* cited by examiner

Flash Corrupted

No Flash

Original                  Flash Correction Applied FIG. 4A                      FIG. 4B

FIG. 5

KALMAN FILTERING FOR FLASH ARTIFACT SUPPRESSION IN ULTRASOUND IMAGING

BACKGROUND

The present embodiments relate to ultrasound-based flow or motion imaging. In ultrasonic blood flow imaging, the signal may include tissue and blood components. The tissue signal components are often 10-100 times stronger than the blood signal components. Estimates of the blood signal power (e.g., power Doppler) and blood velocity (e.g., color Doppler) employ clutter filtering techniques to mitigate signal components that arise from temporally stationary and more slowly moving tissue. These signal components are often referred to as "clutter." Insufficient suppression of clutter produces "flash artifacts," which manifest as regions of false velocity or power in ultrasonic blood flow images. The incomplete removal of clutter results in response from tissue being presented as flow. Flash artifacts may mask true blood velocity and power signals and may make visual assessment more difficult.

Flash artifacts may be detected and reduced. The size, shape, temporal variance, intensity, or location of velocity or power data is used to identify flash. The intensity of pixels characterized as flash artifacts may be removed, reduced, or replaced by another value, but inaccurate detection results in poor suppression. The use of a static intensity threshold in one detection approach is computationally efficient but is not amenable to dynamic environments. Morphological filters, such as min-max processing, in other approaches are also computationally efficient and may adapt to varying environments but exhibit nonlinear characteristics. Techniques that consider spatial characteristics are often not suitable for environments with slowly moving blood flow. Regression techniques, such as polynomial curve fitting, risk overfitting the data.

SUMMARY

By way of introduction, the preferred embodiments described below include a method, system, computer readable medium, and instructions for flash artifact suppression. Kalman filtering, including a model of system dynamics, is used to identify flash artifact. The Kalman filtering predicts the velocity or powers based on a past sequence of velocity or power. The prediction defines a confidence interval. Any current measures surpassing the confidence interval are identified as flash artifact and suppressed.

In a first aspect, a method is provided for flash artifact suppression by an ultrasound scanner. The ultrasound scanner scans a patient at different times. First velocity or power values are estimated from scan data from the scanning of the patient. The velocity or power values represent motion in the patient at the different times. Second velocity or power values are predicted based on the first velocity or power values from prior ones of the different times and based on a model of system dynamics. A statistical confidence interval is determined from the second velocity or power values. The first velocity or power values for a current one of the different times are replaced when the first velocity or power values exceed the statistical confidence interval. The first velocity or power values are replaced with replacement velocity or power values. A flow image is generated on a display from the replacement velocity or power values.

In a second aspect, a method of flash artifact suppression is provided for ultrasound flow imaging. The flash artifact is detected from a predicted flow value of a Kalman filter. The flash artifact is suppressed, and a flow image based on the suppression of the flash artifact is generated on a display.

In a third aspect, an ultrasound system is provided for artifact suppression in ultrasound imaging. A transducer and beamformer is provided for scanning a scan region. A Doppler estimator is configured to estimate, from the scanning, first estimates in the scan region over time. A Kalman filter is configured to predict second estimates from the first estimates. An image processor is configured to detect the artifact in the first estimates from the second estimates and to suppress the artifact in the first estimates. A display is configured to display an image from the first estimates with the artifact suppressed.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Kalman filtering is used for flash artifact detection and suppression in ultrasound motion imaging. The Kalman filter estimates of the state of a process (e.g., state of the velocity or power) at the current timepoint. This estimate is used to generate a confidence interval, within which a measurement of the current state is expected to fall. The confidence interval is compared to the measured velocity or power data at the current timepoint. Measured velocity or power values that exceed the upper bound of the confidence interval have a higher likelihood of having been corrupted by a flash artifact. Thus, the velocities or powers for these locations are removed, reduced, or replaced by another value to suppress the flash.

Post-processing predicts the velocity or power values of pixels within a frame based on measured values of several prior frames and a model of system dynamics. A statistical confidence interval of the sample intensity is generated using the predicted values and a measure of temporal variance over pixels in the prior frames. For each location, the value of the frame is compared to the upper bound of the confidence interval to detect whether the sample has an increased likelihood of being corrupted by flash.

Regions of false velocity or power signals, known as "flash artifacts," arise when tissue is insufficiently suppressed in ultrasound blood flow images. The Kalman filter-based approach detects and removes flash artifacts from image frames. Corrupted samples are detected by comparing a current frame to a confidence interval of expected intensity values. The confidence interval is generated by the temporal variance of prior data and a prediction of the current frame, which is produced by the Kalman filter.

The Kalman filter-based approach handles estimation of a dynamic system state. Using temporal characteristics for flash detection may be more suitable for the detection of flash artifacts than assessment using spatial characteristics. Temporal characteristics are particularly advantageous for microflow applications, which exhibit higher sensitivity to slow moving blood flow. Regions of slow moving blood flow may exhibit spatial characteristics that are similar to flash artifacts, resulting in erroneous suppression. Kalman filtering considers a linear model of system dynamics in addition to measured data. This is beneficial for the estimation of variables that have known temporal variance, such as velocity which varies due to the cardiac or breathing cycle.

Flash artifacts are regions of falsely detected velocity or power data, so flash artifacts may be considered 'false positives.' Suppression using the Kalman filtering may reduce flash artifacts, which enables greater specificity of flow. Greater sensitivity of flow detection may be provided. Conventional frequency domain filters employed during velocity or power image formation often reduce clutter at the expense of sensitivity toward slow moving blood flow. These frequency domain filters may be less aggressive for greater slow flow sensitivity since the Kalman filter-based approach may suppress any resulting flash.

Figure 1:
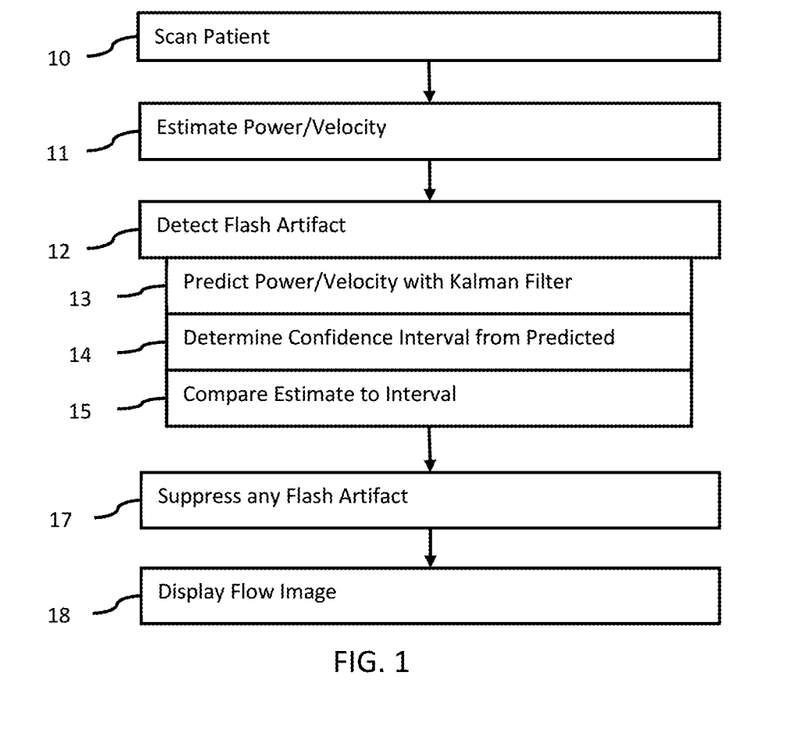
FIG. 1 is a flow chart of one embodiment of a method for flash artifact suppression in an ultrasound system.
Figure 2:
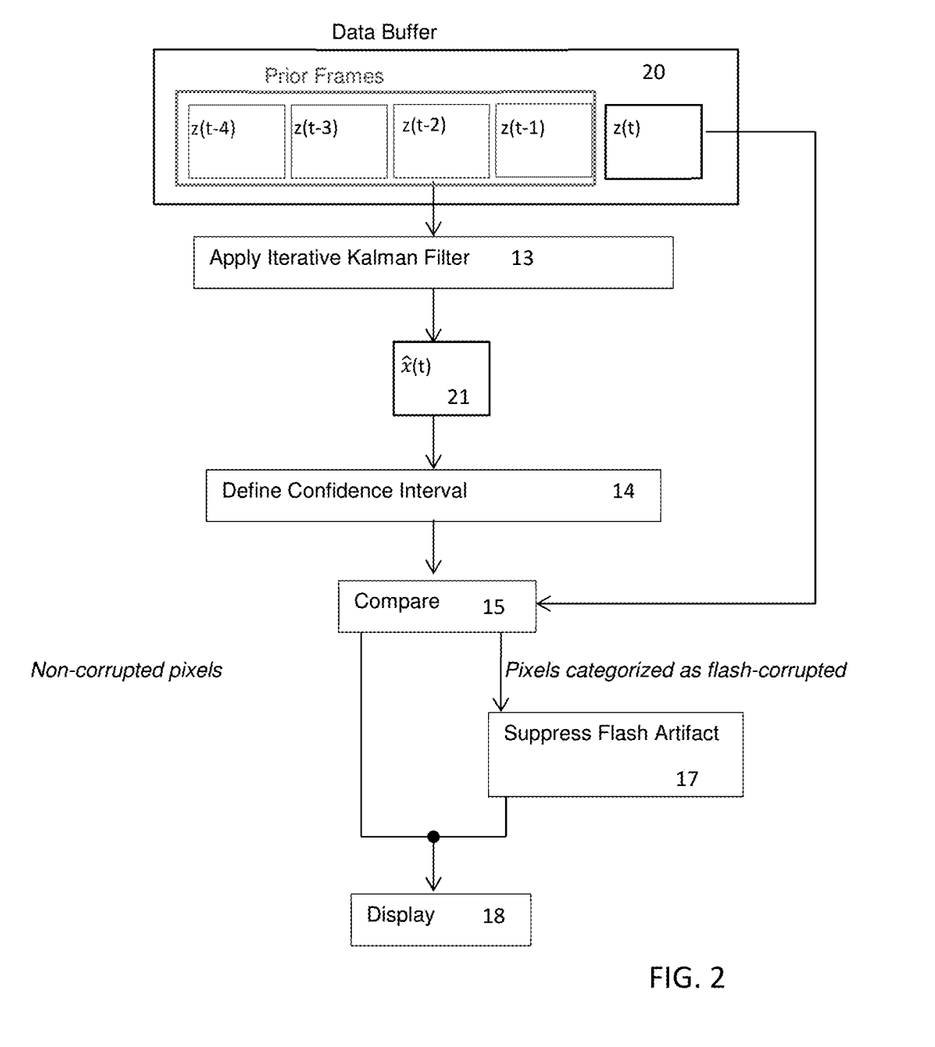
FIG. 2 is a flow chart of another embodiment of a method for flash suppression.

FIG. 1 shows one embodiment of a method for flash artifact suppression for ultrasound flow imaging. Kalman filtering is used to detect flash artifacts. The Kalman filtering includes a model of system dynamics modeling the covariance in the flow estimates. FIG. 2 shows a flow chart of another embodiment of the method for flash suppression with representation of the data resulting from some of the acts. Depending on the length of observation history, iterative or direct Kalman filtering is applied as a post estimation process to suppress flash artifact. Without losing of generality, iterative or iteration in this filing includes direct Kalman filtering where the number of iteration is one.

The method is used for flow imaging, such as power or velocity imaging. Velocity imaging, sometimes referred to as color flow imaging, indicates the motion of blood or other fluid. Power imaging indicates the energy or power returned from moving blood or fluid. The flow imaging provides information over a spatial distribution as compared to spectral imaging or spectral Doppler imaging, where the power spectrum for a range gate is estimated. In flow imaging, the estimated flow for each location is mapped to color for display, providing a spatial representation of motion in a scan region. The "flow" data may not represent color (e.g., may be a scalar). Doppler, color, or flow imaging modes provide color flow imaging. In other embodiments, the motion is of tissue where return from fluids is suppressed. The Kalman filtering may be used to suppress flash in tissue motion imaging.

The methods are implemented in an ultrasound system, such as by an ultrasound scanner or by a computer with access to ultrasound scan data. The methods of FIGS. 1 and 2 are performed by the ultrasound imaging system 50 of FIG. 5, the image processor 59, or a different system and/or processor. For example, an ultrasound scanner as the ultrasound imaging system 50 performs the acts. As another example, the image processor 59 controls a beamformer for scanning in act 10. The Doppler estimator and a wall filter perform flow imaging in act 11 using a beamformer and transducer of the ultrasound scanner. A Kalman filter as a separate device and/or the image processor implementing the Kalman filter performs acts 12-17. A display is used to display a flow image after suppression of flash artifact. A scan converter, graphics memory, temporal filter, and/or other components of an ultrasound scanner may be used in performance of any of the acts.

The acts of FIGS. 1 and 2 are performed in the order shown or a different order. For example, act 10 is repeated as part of act 11.

Additional, different, or fewer acts than shown in FIG. 1 or 2 may be used. For example, act 18 is not performed. In another example, acts 10 and 11 are not provided, such as where a memory provides the estimates of power or velocity as a data buffer 20. In yet another example, acts for user adjustment, original setting, or manual control over the same or different flow imaging parameters are provided.

In act 10, the ultrasound scanner scans a patient. Various locations within a scan region of the patient are scanned with ultrasound. In one embodiment using an ultrasound system, a field of view in a patient is scanned in real-time, providing images while scanning. The scanned region is an interior of an object, such as the patient. The scan is of a volume, plane, or line region. Scanning a plane provides data representing different locations or samples of the plane. The data representing the region is formed from spatial sampling of the object. The spatial samples are for locations distributed in an acoustic sampling grid.

The region for the flow scan may be a region of interest smaller than a field of view or for the entire field of view. The ultrasound system may scan the field of view using B-mode imaging, a combination of B-mode imaging and flow imaging, or other modes of imaging. The flow region is a sub-set of the B-mode field of view. The user or a processor determines the region of interest in which color flow scanning occurs. Alternatively, the color flow region is the full field of view.

Spatial samples along one or more scan lines are received. Where the transmit beam insonifies just one receive scan line, then return or echo samples along that scan line are received. Where the transmit beam insonifies multiple scan lines, then samples along the multiple scan lines may be received simultaneously. To generate the samples for different receive beams at a same time, parallel receive beamformation is performed. For example, a system may be capable of forming two or more, tens, or hundreds of receive beams in parallel. Spatial samples are acquired for a plurality of receive lines in the region of interest in response to one and/or in response to sequential transmit beams.

The scanning may be performed a plurality of times to cover the region. The scanning is repeated to scan different portions of the region of interest. Alternatively, performing one scan acquires the data for the entire region of interest.

For B-mode scanning, the scanning is configured to scan the field of view once for each image or time. Only one transmission along each line is needed for B-mode imaging of the field of view for a given period.

For flow scanning, scan lines in the region of interest are sampled multiple times. The complete region of interest is scanned multiple times in sequence. Scanning in a sequence acquires spatial samples associated with motion. Any now known or later developed pulse sequences and/or scan formats may be used for flow scanning. A sequence of at least two (flow sample count) transmissions is provided along each scan line for flow imaging. For example, the flow sample count is 10-20, resulting in 10-20 samples for each location. Any pulse repetition frequency (i.e., rate of sampling for a location), flow sample count (i.e., number of samples for a location used to estimate), and pulse repetition interval (i.e., time between each sample acquisition for a location) may be used. The samples from the flow sample count are used to determine the flow (e.g., velocity and/or power) at a given time. By adding a sample and removing a sample in a moving window, the flow at a different time is determined. Alternatively, the flow from a different time is provided by adding multiple samples and removing multiple samples (e.g., all or a subset) for the location.

The echo responses to the transmissions or return samples are used to determine intensity for B-mode scanning and estimate velocity, energy (power), and/or variance at a given time for flow imaging. The transmissions along one line(s) may be interleaved with transmissions along another line(s). With or without interleaving, the spatial samples for a given time are acquired using multiple transmissions and receptions over a period to collect the samples of the flow sample count. The estimates from different scan lines may be acquired sequentially, but rapidly enough to represent a same time from a user perspective. Multiple scans are performed to acquire estimates for different times. In flow imaging, scan data for a frame of velocity or power includes sampling from different times or over a period. The resulting frame represents the flow in the patient for a given time or period. By repeating the scanning, frames representing the patient at different times are formed.

In alternative embodiments, the return samples (e.g., B-mode data and/or flow data) are acquired by transfer over a network and/or loading from memory. Data previously acquired by scanning, such as beamformed samples prior to estimation or estimates, is acquired.

In act 11, a Doppler estimator (e.g., Doppler processor) estimates velocity or power values from the scan data from the scanning of the patient. For flow imaging, an estimator or detector generates flow data representing locations in the patient. Flow data includes estimates of velocity, energy (e.g., power), and/or variance. The flow data may be for fluid, but alternatively motion data for tissue is estimated. Any motion data, whether from fluid or tissue movement, may be acquired.

The received spatial samples may be clutter filtered prior to estimation. The clutter filter passes frequencies associated with fluid and not tissue motion or with tissue motion and not fluid. The clutter filtering is of signals in the pulse sequence for estimating motion at a given time (e.g., samples of a flow sample count). A given signal may be used for estimates representing different times, such as associated with a moving window for clutter filtering and estimation. Different filter outputs are used to estimate motion for a location at different times. As further scans occur, further clutter filtering and estimation creates frames of estimates for different times.

Doppler processing, such as autocorrelation, may be used. In other embodiments, temporal correlation may be used. Another process may be used to estimate the flow data. Doppler parameter values (e.g., velocity, energy, or variance values) are estimated from the spatial samples acquired at different times. The change in frequency (e.g., Doppler shift) between two samples for the same location at different times indicates the velocity. A sequence (flow sample count) of two or more samples may be used to estimate the Doppler parameter values. Estimates are formed for different groupings of received signals, such as completely separate or independent groupings or overlapping groupings. The estimates for each grouping represent the spatial location at a given time. Frames of velocity and/or power values are formed for different times.

Values representing the different locations are included in each frame. The estimation is performed for the different sampled spatial locations. For example, velocities for the different locations in a plane are estimated from echoes responsive to the scanning. Multiple frames of flow data are acquired to represent the same locations in a region of interest at different times.

The estimates may be thresholded. Thresholds are applied to the velocities and/or powers. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities or powers are used without thresholding.

The acquired motion or flow data is a frame of data or image representing the patient at a given time, despite being estimated from received signals over the flow sample count. The frames from different times may be temporally filtered, such as using an infinite or a finite impulse response.

Other data may be generated, such as B-mode data. A B-mode image may be overlaid with or have an incorporated region of interest showing the Doppler velocities or powers. Within the region of interest, locations with no flow are shown as B-mode data.

This front-end or upstream data processing produces a sequence of frames of velocity and/or power data. The data contained in each frame represents blood flow velocity or blood signal power and may be corrupted by flash artifacts. As shown in FIG. 2, a number of successively acquired frames are stored in a circular or other buffer or memory 20. For example, the buffer 20 may contain the current frame and four prior frames. In other examples, frames over half a second, such as 5-10 frames, are stored in a first-in first-out arrangement. A greater number of frames over the same or long period may be used. For a given temporal window in the five-frame example, this acquired data may be represented as:

$$z=\{z(t),z(t-1),z(t-2),z(t-3),z(t-4)\}$$

where z is a frame of measured velocity or power estimates, and t is time (five times from t−4 to current time t) so that five frames from five different times are buffered.

The objective of the process is to determine if any of the velocity or power values within the current frame, z(t), are corrupted by a flash artifact. The values for a sub-set or all the spatial locations in a frame may not be corrupted by flash. The values for a sub-set or none of the spatial locations may be corrupted by flash. The values for each spatial location are checked for corruption location-by-location using the velocity or power estimates for the same location from the current frame and past frames.

In act 12, an image processor detects the flash artifact. The detection is of whether a current velocity or power value for a current frame (e.g., z(t)) is corrupted by flash. The detection relies on a flow value (e.g., velocity or power) predicted by a Kalman filter. Using the previous flow values from previous frames with or without the current value, the Kalman filter predicts a flow value for the current frame. The Kalman filter uses a model of the system dynamics for its prediction. The system dynamics are of the system represented by the sequence of frames. The sequence of estimates is modeled for prediction. This model includes scanner as well as patient influence on the values by modeling the sequence of values from the patient by the scanner in an on-going manner.

Figure 3A:
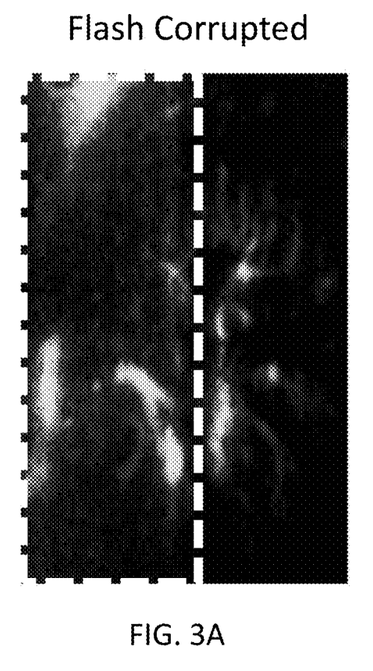
FIGS. 3A and 3B show example flash corrupted and no flash corruption color flow images (shown in gray scale)
Figure 3B:
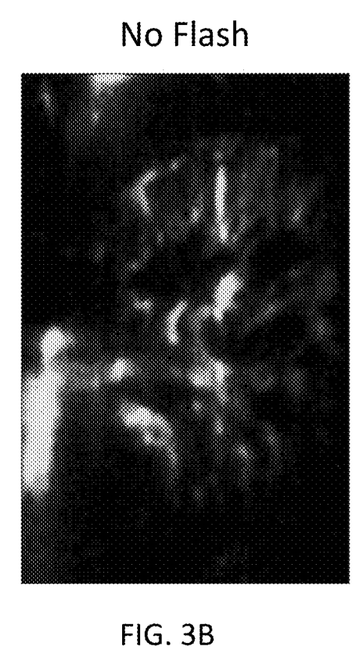

For the prediction, it is assumed that the acquired dataset {z} is a noisy measure of the true velocity or power, {x}. FIG. 3A shows a flow image with flash corruption, such as resulting from imaging with z(t). FIG. 3B shows an image without flash corruption, such as imaging with true flow, x(t). Kalman filtering is employed to generate a de-noised estimate of the true velocity or power, denoted {2}.

The Kalman filtering to predict a value of the current flow is an iterative approach. The iteration progresses through the buffer. As the temporal window selects different sets of frames of data in an on-going or first-in first-out manner, the Kalman filtering repeats. Kalman filtering is applied iteratively. The most antecedent data frame in the buffer is processed in the first iteration. The Kalman processing yields the de-noised estimate of the frame as the predicted values. In the example of FIG. 2, z(t−4) is processed first, yielding the de-noised estimate, x̂(t−4). In the second iteration, the next data frame (e.g., z(t−3)) in the buffer is processed, using the de-noised estimate produced in the first iteration as a statistical prior. z(t−3) is processed, using x̂(t−4) as a statistical prior to generate the de-noised estimate, x̂(t−3). The remaining data in the buffer is iteratively processed using the same technique. This yields a de-noised estimate, x̂(t), of the data in the current frame, z(t). As a next "current" frame is acquired, then the frames in the buffer 20 shift. The prediction for the new estimate uses the already predicted estimates for the four or other frames still in the buffer 20.

Acts 13-15 show one example detection of the flash artifact. The prediction of act 13 is used to determine a confidence interval in act 14. The current measure or estimate is compared to the confidence interval in act 15 to detect whether the current estimate is corrupted by flash. Additional, different, or fewer acts using Kalman filtering may be used.

In act 13, the image processor, Kalman filter, or other circuit predicts velocity or power values based on the measured velocity or power values from prior ones of the different times and based on a model of system dynamics. Values are predicted for different locations for each of the different times. As each new frame of values is estimated, values for the different locations represented by the frame are predicted. Due to anatomical heterogeneity, the Kalman filtering is performed on a location-by-location basis. The prediction is performed independently such that a prediction is performed for each location. The data from different locations may be used to independently or cohesively determine the predicted value for a given location. Different groupings of locations and corresponding values are used for the different locations, such as with a moving window or filter kernel.

The Kalman filter models the system dynamics. This model includes a state model with process noise and a measurement model with measurement noise. Kalman filtering is a Bayesian technique that derives an estimate of the current state of a process recursively using an ensemble of measurements and a model of system dynamics. The model of system dynamics is described by two equations: the state equation, which describes the dynamics of the process being studied, and the measurement equation, which describes the dynamics involved in the measurement of the process.

For example, if the data represents the blood signal power, the state and measurement equations may be described as follows. The blood signal power is known to be a measure of the scattering coefficient of the blood signal. For a short ensemble of frames, the signal power is modeled as a constant. Thus, the state equation is:

$$x(t)=x(t-1)+w(t),$$

where the blood power in the current frame, x(t), is a function of the blood power in the prior frame, x(t−1). The signal to be produced by process noise, w(t), varies. The process noise incurs a random walk in the neighborhood of correlated locations and number of frames for defining the covariance. Additionally, the process noise covariance, Q, is defined as $[w(t)w(t)^T]$, where T indicates the conjugate transpose.

The measurement of the blood signal power is an accurate approximation of the true power. Thus, the measurement equation is:

$$z(t)=x(t)+v(t).$$

where the measured blood power at the current frame, z(t), is a function of the true blood power, x(t). Measurement variation is attributed to measurement noise, v(t). Additionally, the measurement noise covariance, R, is defined as $[v(t)v(t)^T]$, where T indicates the conjugate transpose.

Other state and measurement equations may be used for blood power. For blood velocity, the state equation may include one or more additional variables to account for acceleration, turbulence, or other flow characteristics. Rather than assuming constant in the short period, one or more variables in addition to the noise may vary for either power or velocity, such as to account for heart cycle and/or breathing cycle variation. Since clutter often occurs in non-flow locations, using constants may not need to account for physiological variation.

In addition to process and measurement noises, an error covariance contributes to variation. To predict with the process noise, the measurement noise, and the error covariance, a temporal variance in the measured values over time is used. The temporal variance is calculated, and this variance is divided between the noises and error covariance. Any division may be used, such as assigning equal or unequal parts of the variance to the noises and error covariance. The noises and error covariance are set for each location based on the temporal variance in the measured estimates for the respective location. This setting is an initialization of the prediction by Kalman filtering.

In one embodiment, Kalman filtering initializes estimates of the process noise covariance, Q, and the measurement noise covariance, R. Additionally, initial values for the underlying state, x(t), and the estimate error covariance, P, are set. The error covariance, P, describes the confidence level of the estimate. The initial estimate of the underlying state may be defined as the average measured across the prior data frames held in the buffer 20. The initial true state values, x(t), may be a mean of measured values for a surrounding neighborhood of location including or not including the location being initialized. P, Q, and R may be defined as functions of the temporal variance measured across prior data. Any function may be used, such as empirically weighting or dividing the variance amongst P, Q, and R. Other sources of initial values, such as defaults, temporal averages, and/or spatial averages may be used.

The Kalman filter is iteratively applied to estimate the true state of the process at each timepoint, starting at the most antecedent frame. Kalman filtering is considered to be recursive because the estimate for a specified timepoint relies on the estimate generated in the previous timepoint. Each iteration involves two conceptual phases: a prediction phase and a measurement phase. In a prediction phase after initialization, prior state estimates and prior error covariance are used. In a measurement phase with Kalman gain, a current state estimate is predicted, and the error covariance is updated. The state is recursively estimated.

In one embodiment of the prediction phase, the Bayesian prior estimates of the state and error covariance are defined. These values are inferred from the prior estimate and the model of system dynamics. For the first iteration, there are no prior estimates, so the priors are initialized. For subsequent iterations, the model of system dynamics is used. In the example of blood power, the prior phase may be:

$$\hat{x}(t)^- = \hat{x}(t-1) \qquad \text{Prior state estimate}$$

$$P(t)^- = P(t-1) + Q \qquad \text{Prior error covariance}$$

where the bar (⁻) indicates the variable being defined as a Bayesian prior. Other prediction functions may be used.

In the measurement phase, the prior estimates are combined with the measurement of the process, which is used to produce an estimate of the true process at the current timepoint. The relative weight given to the model-derived prior estimate and measured estimate is statistically defined using the Kalman gain, K. For example, the measurement phase may be:

$$K = P(t)^- \text{inv}(P(t)^- + R) \qquad \text{Kalman gain}$$

$$\hat{x}(t) = \hat{x}(t)^- + K(z(t) - \hat{x}(t)^-) \qquad \text{State estimate}$$

$$P(t) = (I-K)P(t)^- \qquad \text{Error covariance update}$$

where I denotes the identity matrix. Other equations may be used.

At the end of the iteration for the specified timepoint, an estimate of the true state is produced as the state estimate (i.e., predicted value $\hat{x}(t)$) and the error covariance is updated. The iteration outputs a predicted estimate based on the model of system dynamics. The values from the current iteration are used to inform the estimate of the state at the next timepoint iteration. This Kalman filtering-based prediction process is iteratively repeated for all frames held in the buffer 20, resulting in an estimate, $\hat{x}(t)$ 21, of the state for the current timepoint. Another iteration occurs as each new "current" frame is added to the buffer 20.

In act 14, the image processor, Kalman filter, or other processor determines a statistical confidence interval from the predicted velocity or power value. The statistical confidence interval is determined for each location from the predicted flow estimate (e.g., predicted true value, $\hat{x}(t)$ 21) for that location. The determination is performed for each iteration (i.e., for each time).

The statistical confidence interval is a range of values encompassing the expected or likely possible true values. Any interval or range may be used, such as one or two standard deviations. For example, the range is for 95% confidence using two standard deviations of the measured velocity or power values (e.g., z) over the different times.

In one embodiment, the confidence interval describing the expected distribution of values over time is constructed using the de-noised estimate, $\hat{x}(t)$, and standard deviation, a. The standard deviation may be obtained from a measure of the temporal variance over the frames, z, held in the buffer 20 or over the predicted values, x, from different times. For example, a 95% confidence interval for normally distributed measured estimates, z, is defined as:

$$CI_{95} = \hat{x}(t) \pm 2\sigma.$$

Flash artifacts are often characterized by a relatively high intensity excursion from prior data frames. Thus, values for locations that exceed the upper bound of the respective confidence intervals have an increased likelihood of being corrupted by a flash artifact.

In act 15, the image processor, Kalman filter, or other processor compares the measured flow value to the confidence interval. The estimated values within the current frame, z(t), are compared against the respective confidence intervals location-by-location. As shown in FIG. 2, any flow estimates within the respective confidence intervals are passed on for imaging without suppression. Any flow estimates exceeding the upper bounds defined by the respective confidence intervals are classified as corrupted by flash artifact. Any flow estimates exceeding the lower bound are replaced with the estimated value, other statistics from prior knowledge or observation, or no change.

In act 17, the image processor, Kalman filter, or other processor suppresses the flash artifact. Corrupted flow estimates may be removed, reduced, or replaced by other values. For example, a velocity or power value identified as corrupted is replaced with the predicted value, $\hat{x}(t)$ or another value within the confidence interval (e.g., high corrupted value replaced with a value one standard deviation from the predicted value). As another example, a default or average from non-corrupted values in a spatial neighborhood at the same time is used. In yet another example, the velocity or power value is zeroed or removed to indicate no flow. In another example, a measured or predicted flow value from a different time or frame or an average over time is used to replace the corrupted value. Any replacement power or velocity value may be used.

The suppression is performed for each of the locations. The velocity or power value for each location in the current frame is suppressed or not based on the comparison of act 15. The replacement occurs for some locations and not other locations. The replacement occurs where flash is identified and does not occur where flash is not identified for a given current frame of flow values.

Once corrupted values and corresponding locations are processed, the current frame, with any replacement values, is passed to subsequent processing and display. In act 18, the flow image is displayed. The ultrasound system or image processor processes the frame of flow data to create the image. Spatial filtering, temporal filtering, scan conversion, or another image process is performed. The scalar values are mapped to display values, such as mapping to color values using a velocity scale. The resulting image is buffered for display. The display values are provided from the buffer to the display.

Flow (e.g., Doppler energy and/or Doppler velocity), Doppler tissue motion, or other motion image is generated. The image may include other information. For example, the image is an overlay of the flow data on B-mode data. For non-tissue locations or locations associated with sufficient flow, the flow data (e.g., velocities) are used to determine a color to display. For tissue locations or low/no flow locations, the B-mode data is used.

The image uses none or some values replaced due to flash corruption. Other or all values as measured (e.g., z(t) or color mapped from z(t)) are used. For example, one or more spatial locations included corrupt flow values, so replacement values are used to generate the image for those locations. Other spatial locations were not corrupted by flash, so the measured values are used to generate the image for those locations. The flow image is generated on a display based on the suppression of the flash artifact.

Figure 4A:
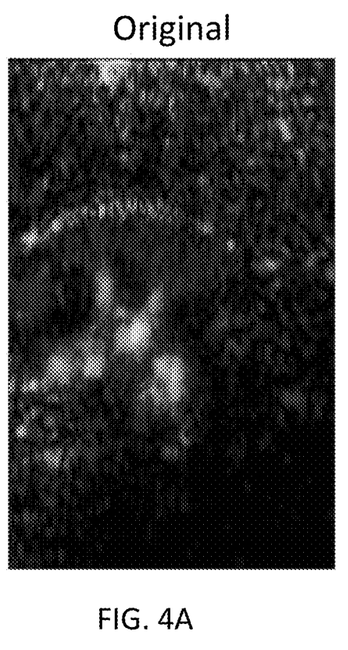
FIGS. 4A and 4B show example flash corrupted and Kalman filter-based suppression color flow images (shown in gray scale)
Figure 4B:
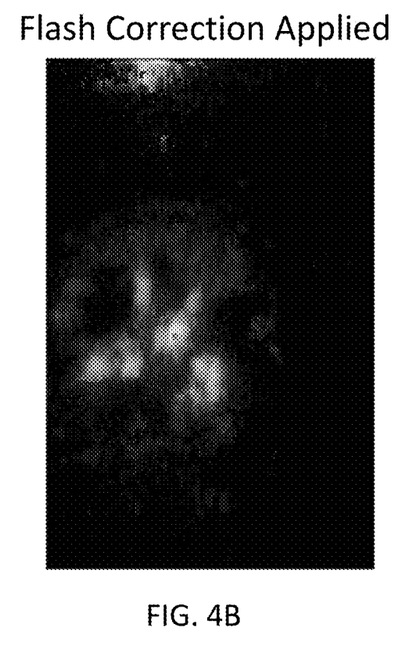

FIG. 4A shows a flow image with flash corruption. FIG. 4B shows the same image with the flash suppressed using Kalman filtering-based detection of the flash and replacement by the Kalman-filter predicted value. A preset value, mean of observation, or weighted average may be used.

The iterative Kalman filtering continues. As each new frame of velocity or power estimates is generated from scanning and estimation, flash suppression is applied for that frame. A flow image based on that frame as flash suppressed is displayed. A sequence of flash suppressed flow images is displayed where each flow image represents the patient at a different time (i.e., for different periods of the respective flow sample counts).

Figure 5:
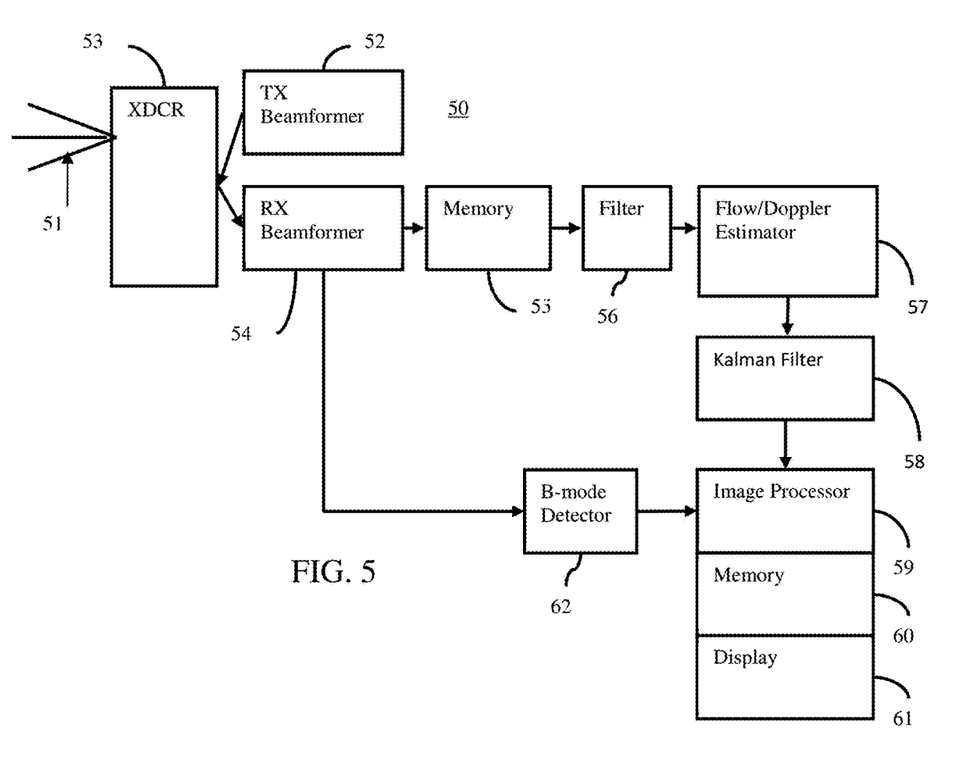
FIG. 5 is a block diagram of one embodiment of a system for flash suppression.

FIG. 5 shows one embodiment of an ultrasound system 50 for artifact suppression in ultrasound imaging. Flash or other artifacts in flow or motion imaging are suppressed using the Kalman filter 56.

The system 50 implements the method of FIG. 1, the method of FIG. 2, or another method. The system 50 includes a transmit beamformer 52, a transducer 53, a receive beamformer 54, a memory 55, a filter 56, a flow estimator 57, a Kalman filter 58, an image processor 59, another memory 60, a display 61, and a B-mode detector 62. Additional, different or fewer components may be provided. For example, the flow estimator 57 and image processor 59 are provided without the front-end components, such as the transmit and receive beamformers 12, 16. In yet another example, the memories 18 and 28 are one component. As another example, the Kalman filter 58 and image processor 59 are implemented as one device performing both operations.

In one embodiment, the ultrasound system 50 is a medical diagnostic ultrasound system. In an alternative embodiment, the ultrasound system 50 is a computer or workstation operating on ultrasound data. In yet another embodiment, the flow estimator 57 is part of a medical diagnostic ultrasound system or another medical imaging system, and the image processor 59 is part of a separate workstation, server, or remote system.

The transducer 53 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 53 connects with the transmit beamformer 52 and the receive beamformer 54 through a transmit/receive switch, but separate connections may be used in other embodiments.

The transmit and receive beamformers 52, 54 are a beamformer for scanning a region of the patient with the transducer 53. The transmit beamformer 52, using the transducer 53, transmits one or more beams to scan a region. Vector®, sector, linear or other scan formats may be used. The receive lines and/or transmit beams are distributed in the scan region. The receive beamformer 54 samples the receive beams at different depths. Sampling the same locations at different times obtains a sequence for flow estimation.

The transmit beamformer 52 is a processor, delay, filter, waveform generator, memory, phase rotator, digital-to-analog converter, amplifier, combinations thereof or any other now known or later developed transmit beamformer components. In one embodiment, the transmit beamformer 52 digitally generates envelope samples. Using filtering, delays, phase rotation, digital-to-analog conversion, and amplification, the desired transmit waveform is generated. Other waveform generators may be used, such as switching pulsers or waveform memories.

The transmit beamformer 52 is configured as a plurality of channels for generating electrical signals of a transmit waveform for each element of a transmit aperture on the transducer 53. The waveforms are unipolar, bipolar, stepped, sinusoidal or other waveforms of a desired center frequency or frequency band with one, multiple, and/or fractional number of cycles. The waveforms have relative delay and/or phasing and amplitude for focusing the acoustic energy. The transmit beamformer 52 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and/or combinations thereof. A transmit beam focus is generated based on these beamforming parameters.

The receive beamformer 54 is a preamplifier, filter, phase rotator, delay, summer, base band filter, processor, buffers, memory, combinations thereof or other now known or later developed receive beamformer components. The receive beamformer 54 is configured into a plurality of channels for receiving electrical signals representing echoes or acoustic energy impinging on the transducer 53. A channel from each of the elements of the receive aperture within the transducer 53 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form return samples for one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 54 is configured to form receive beams in response to the transmit beams. For example, the receive beamformer 54 receives one, two, or more receive beams in response to each transmit beam. The receive beams are collinear, parallel and offset or nonparallel with the corresponding transmit beams. The receive beamformer 54 outputs spatial samples representing different spatial locations of a scanned region. Once the channel data is beamformed or otherwise combined to represent spatial locations along the scan lines 51, the data is converted from the channel domain to the image data domain. The phase rotators, delays, and/or summers may be repeated for parallel receive beamformation. One or more of the parallel receive beamformers may share parts of channels, such as sharing initial amplification.

For B-mode scanning, the intensity of the echo for each location is determined by the B-mode detector 62. The field of view is scanned by sampling each location once to provide a frame of B-mode data for a given time.

For imaging motion, such as tissue motion or fluid motion, multiple transmissions and corresponding receptions are performed for each of a plurality of substantially same spatial locations. Substantially is used to account for intervening transducer or patient motion. Phase changes between the different receive events for each given location indicate the velocity of the tissue or fluid. A velocity sample group corresponds to multiple transmissions for each of a plurality of scan lines 51. The number of times a substantially same spatial location, such as a scan line 51, is scanned within a velocity sample group is the velocity or flow sample count. The transmissions for different scan lines 51, different velocity sample groupings or different types of imaging may be interleaved. The amount of time between transmissions to a substantially same scan line 51 within the velocity sample count is the pulse repetition interval. The pulse repetition interval establishes the pulse repetition frequency or vice versa.

The memory 55 is video random-access memory, random access memory, removable media (e.g. diskette or compact disc), hard drive, database, corner turning memory, or other memory device for storing data or video information. In one embodiment, the memory 55 is a corner turning memory of a motion parameter estimation path. The memory 55 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid. The return samples of the flow sample count for each of a plurality of locations are stored.

The filter 56 is a clutter filter, finite impulse response filter, infinite impulse response filter, analog filter, digital filter, combinations thereof or other now known or later developed filter. In one embodiment, the filter 56 includes a mixer to shift signals to baseband and a programmable low pass filter response for removing or minimizing information at frequencies away from the baseband. In other embodiments, the filter 56 is a low pass, high pass, or band pass filter. The filter 56 reduces signals from fluids or alternatively reduces the influence of signal from tissue while maintaining velocity information from fluids. The filter 56 has a set response or may be programmed, such as altering operation as a function of signal feedback or other adaptive process. In yet another embodiment, the memory 55 and/or the filter 56 are part of the flow estimator 57.

The Doppler or flow estimator 57 is a Doppler processor or cross-correlation processor for estimating the flow or motion data. In alternative embodiments, another device now known or later developed for estimating velocity, power (e.g., energy), and/or variance from any or various input data may be provided. The flow estimator 57 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and/or variance may also be calculated.

Flow or motion data (e.g., velocity, power, and/or variance) is estimated for spatial locations in the scan region from the beamformed scan samples. For example, the velocity or power estimates represent a plurality of different locations in a plane. The estimates are motion data for tissue and/or fluid.

The Doppler estimator 57 may apply one or more thresholds to identify sufficient motion information. For example, velocity and/or power thresholding for identifying velocities is used. In alternative embodiments, a separate processor or filter applies thresholds. In other embodiments, the thresholding is applied after any motion suppression, such as by the image processor 59.

The flow estimator 57 outputs frames of data representing the scan region at different times. The beamformed samples for a given flow sample count are used to estimate for a time. A moving window with overlap of the data is used to estimate for other times. Velocities for each location at different times are output.

The Kalman filter 58 is a circuit, processor, application specific integrated circuit, field programmable gate array, or other device for performing Kalman filtering. In one embodiment, the Kalman filter 58 includes a memory for the buffer 20 and/or accesses the memory 60 for buffering. The Kalman filter 58 may be implemented by the image processor 50.

The Kalman filter 58 is configured by software, hardware, design, or firmware to predict estimates for different locations. For each location, prior estimates are used for prediction of a noise or flash free Doppler power or velocity. The actual measured estimates are used for initialization, variance calculation, and/or state estimation. The Kalman filter is a model of system dynamics including noise and error covariance. The noise and error covariance are initialized by assignment from variance in the measured estimates over time. The state and measurements are used in prediction and measurement phases to generate a predicted estimate free of flash corruption for each location.

The image processor 59 is a digital signal processor, a general processor, an application specific integrated circuit, field programmable gate array, control processor, digital circuitry, analog circuitry, graphics processing unit, filter, combinations thereof or other now known or later developed device for detecting and suppressing flash. The image processor 59 operates pursuant to instructions provided in the memory 60 or a different memory. The image processor 59 is one or more devices, such as a network of processors using parallel or sequential processing. The image processor 59 is configured by software, firmware, and/or hardware.

The image processor 59 receives B-mode data and/or estimates from the B-mode detector 62, Doppler estimator 57, the memory 60, and/or another source. Using the received data, the image processor 59 is configured to detect the flash artifact in the estimates from the Doppler estimator 57. The detection uses the estimates predicted by the Kalman filter 58. A confidence interval based on variance of the estimates and the predicted flash free estimate is determined. The confidence interval may be any number of standard deviations based on the variance of the measured estimates. The confidence interval is based on deviation from the predicted estimate of the Kalman filter 58. The measured estimates from the Doppler estimator 57 are compared to the confidence interval. Any estimates exceeding a range of the confidence interval are identified as corrupted by flash.

The image processor 59 is configured to suppress the artifact in the corrupted estimates and not suppress or suppress less in non-corrupted estimates. The suppression replaces the value of the measured estimates. The replacement may be by removal, reduction, or substitution. In one example, the image processor 59 replaces the corrupted estimate with the predicted flash-free estimate from the Kalman filter 58.

The image processor 59 or other component uses the estimates to generate an image. Since some of the estimates have flash suppressed by replacement, the resulting image has less flash artifact. The frame is scan converted and color mapped. The resulting color values are added to a B-mode image, such as an overlay, or used alone. The color values are placed in a display buffer to display an image on the display 60.

The display 60 is a CRT, LCD, plasma, projector, monitor, printer, touch screen, or other now known or later developed display device. The display 60 receives RGB, other color values, or other flow or motion values and outputs an image. The image may be a gray scale or color image. The image represents the region of the patient with greater diagnostic information content due to the flash suppression. The display 60 displays a Doppler or other color image from the estimates with the flash artifact suppressed. FIG. 4B shows an example image with flash suppression (compare to FIG. 4A).

The memory 60 is video random-access memory, random access memory, removable media (e.g. diskette or compact disc), hard drive, database, or other memory device for storing color or other motion data. The stored data is in a polar or Cartesian coordinate format. The memory 60 is used by the image processor 59 and/or Kalman filter 58 for system modeling, prediction, buffering, variance determination, covariance operations, storing the image, and/or configuration.

The instructions for implementing the processes, methods and/or techniques discussed above are provided on computer-readable storage media or memories, such as a cache, buffer, RAM, removable media, hard drive or other computer readable storage media. The memory 60 or other memory stores the instructions for flash suppression in Doppler imaging. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for flash artifact suppression by an ultrasound scanner, the method comprising:
   scanning, by the ultrasound scanner, a patient at different times;
   estimating first velocity or power values from scan data from the scanning of the patient, the velocity or power values representing motion in the patient at the different times;
   predicting second velocity or power values based on the first velocity or power values from prior ones of the different times and based on a model of system dynamics;
   determining statistical confidence intervals from the second velocity or power values;
   replacing the first velocity or power values for current ones of the different times when the first velocity or power values exceed the statistical confidence intervals, the first velocity or power values replaced with replacement velocity or power values; and
   generating a flow image, on a display, from the replacement velocity or power values.

2. The method of claim 1 wherein estimating the first velocity or power values comprises estimating flow velocities at different locations for each of the different times, and wherein generating the flow image comprises generating the flow image as one of a plurality of velocity images for the different times, each of the velocity images being based on the predicting and determining for the respective one of the different times and representing the different locations.

3. The method of claim 1 wherein estimating the first velocity or power values comprises estimating flow powers at different locations for each of the different times, and wherein generating the flow image comprises generating the flow image as one of a plurality of power images for the different times, each of the power images being based on the predicting and determining for the respective one of the different times and representing the different locations.

4. The method of claim 1 wherein predicting comprises predicting with a Kalman filter.

5. The method of claim 1 wherein predicting comprises predicting the second velocity or power values for different locations at each of the different times, the predicting for each of the different locations being performed independently of the predicting for others of the different locations.

6. The method of claim 1 wherein predicting comprises predicting based on the model of the system dynamics comprising a state model and a measurement model with process noise and measurement noise, respectively.

7. The method of claim 6 wherein predicting comprises predicting with the process noise, the measurement noise, and an error covariance set based on a temporal variance in the first velocity or power values for a location over the different times.

8. The method of claim 1 wherein predicting comprises predicting in a prediction phase with a prior state estimate and a prior error covariance and in a measurement phase with a Kalman gain, a current state estimate, and an error covariance update.

9. The method of claim 1 wherein determining comprises determining a range within two standard deviations of the first or second velocity or power values over the different times.

10. The method of claim 1 wherein replacing comprises replacing for some locations represented by the first velocity or power values and not other locations, and wherein generating comprises generating the flow image from the replacement velocity or power values for the some locations and from the first velocity or power values for the other locations.

11. A method of flash artifact suppression for ultrasound flow imaging, the method comprising:
    detecting the flash artifact from a predicted flow value of a Kalman filter;
    suppressing the flash artifact; and
    generating a flow image on a display, the flow image based on the suppression of the flash artifact.

12. The method of claim 11 wherein detecting comprises predicting the flow value from previous values by the Kalman filter, and wherein generating the flow image comprises generating the flow image with the flash artifact suppressed for one of a plurality of locations.

13. The method of claim 11 wherein detecting comprises predicting by the Kalman filter comprising a model of system dynamics.

14. The method of claim 11 wherein detecting comprises comparing a measured flow value to a confidence interval from the predicted flow value and at least one standard deviation.

15. The method of claim 11 wherein suppressing comprises replacing a measured flow value with the predicted flow value.

16. An ultrasound system for artifact suppression in ultrasound imaging, the ultrasound system comprising:
    a transducer and beamformer for scanning a scan region;
    a Doppler estimator configured to estimate, from the scanning, first estimates in the scan region over time;
    a Kalman filter configured to predict second estimates from the first estimates;
    an image processor configured to detect the artifact in the first estimates from the second estimates and to suppress the artifact in the first estimates; and
    a display configured to display an image from the first estimates with the artifact suppressed.

17. The ultrasound system of claim 16 wherein the first and second estimates comprise Doppler power or velocity estimates.

18. The ultrasound system of claim 16 wherein the Kalman filter comprises a model of system dynamics with noise and error covariance being assigned from variance of the first estimates over time.

19. The ultrasound system of claim 16 wherein the image processor is configured to detect the artifact with a confidence interval of the second estimates and a standard deviation of the first estimates over time.

20. The ultrasound system of claim 16 wherein the image processor is configured to suppress the artifact by replacement of one of the first estimates with one of the second estimates.

* * * * *